United States Patent [19]
Manley

[11] 3,964,469
[45] June 22, 1976

[54] DISPOSABLE ELECTRODE

[75] Inventor: Arthur G. Manley, Andover, Mass.

[73] Assignee: Eastprint, Inc., Andover, Mass.

[22] Filed: Apr. 21, 1975

[21] Appl. No.: 570,077

[52] U.S. Cl. .............................. 128/2.1 E; 128/417; 128/DIG. 4
[51] Int. Cl.² ........................................... A61B 5/04
[58] Field of Search ............ 128/2.06 E, 2.1 E, 404, 128/410, 411, 416–418, DIG. 4

[56] References Cited
UNITED STATES PATENTS

| | | | |
|---|---|---|---|
| 3,701,346 | 10/1972 | Patrick, Jr. et al. | 128/2.06 E |
| 3,805,769 | 4/1974 | Sessions | 128/2.06 E |
| 3,828,766 | 8/1974 | Krasnow | 128/2.1 E |
| 3,830,229 | 8/1974 | Johnson | 128/2.06 E |
| 3,845,757 | 11/1974 | Weyer | 128/2.06 E |
| 3,865,099 | 2/1975 | Robichaud | 128/2.1 E |
| 3,868,946 | 3/1975 | Hurley | 128/2.1 E |
| 3,882,853 | 5/1975 | Gofman et al. | 128/2.06 E |

Primary Examiner—Robert W. Michell
Assistant Examiner—Lee S. Cohen
Attorney, Agent, or Firm—Cesari and McKenna

[57] ABSTRACT

A premoistened disposable electrode has a flexible conforming base layer with an opening extending between its top surface and an adhesive-coated bottom surface. A flexible, resilient collar extends around the opening at the bottom surface of the base layer and a flexible, resilient gel pad is snugly received in that opening. The upper surface of the gel pad is contacted by a silver-plated plastic snap fastener eyelet which is press-fit into a conventional metal snap fastener stud, the two supported by a thin plastic sheet adhered to the top surface of the base layer.

7 Claims, 3 Drawing Figures

U.S. Patent June 22, 1976 3,964,469
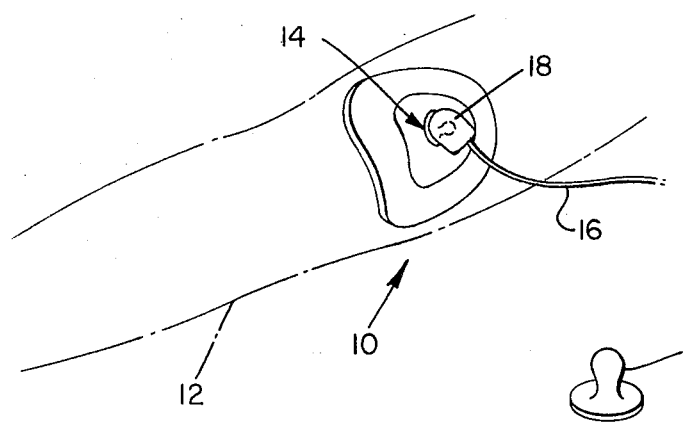
FIG. 1
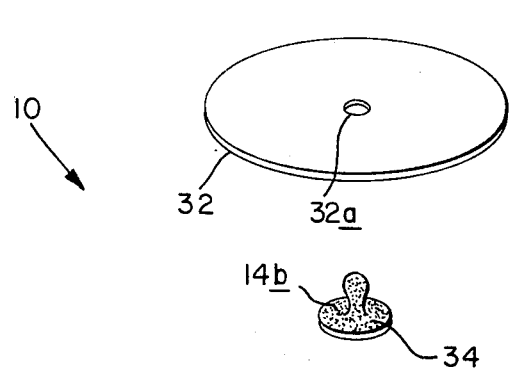
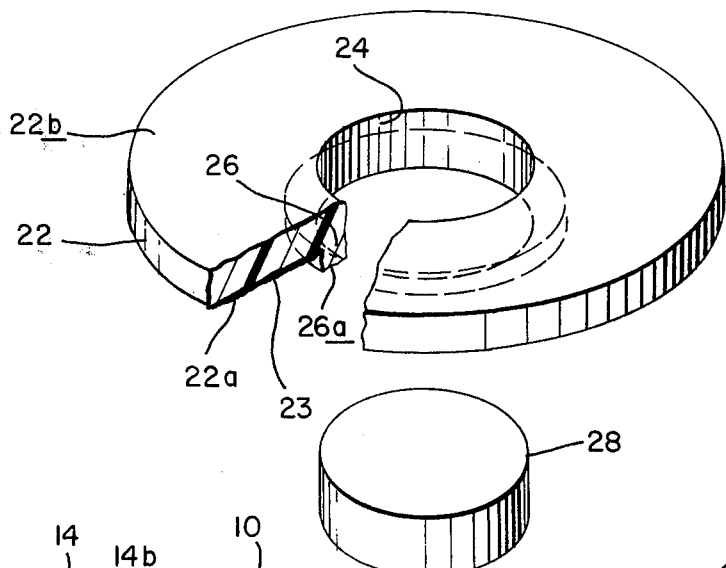
FIG. 2
FIG. 3
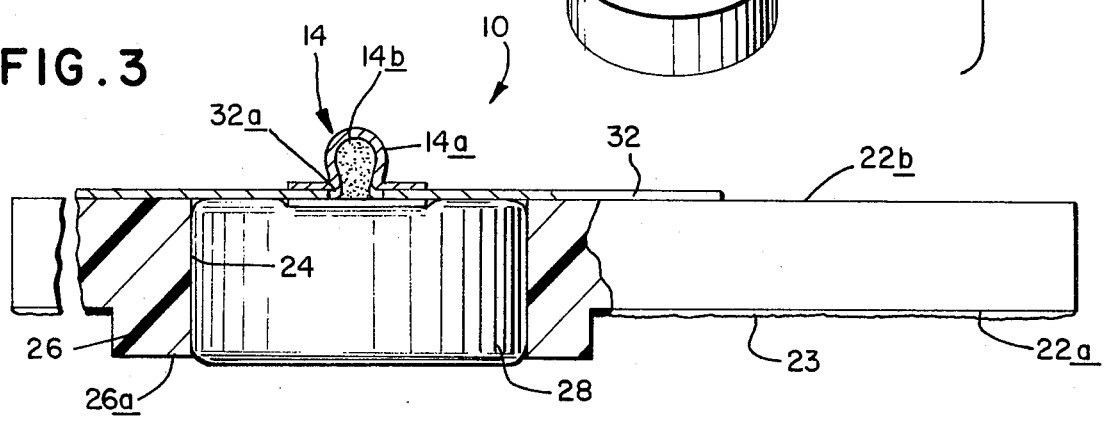

DISPOSABLE ELECTRODE

BACKGROUND OF THE INVENTION

This invention relates to a medical electrode. It relates more particularly to a disposable premoistened electrode for adherence to a patient's body to provide conductive contact between an area of the patient's skin underlying the electrode and apparatus for monitoring electrical signal originating in the patient's body.

To maximize the strength of the body signals applied to the monitoring apparatus, it is essential that a good conductive path be provided between the electrical lead coupled to the electrode and leading to the monitoring apparatus and the patient's skin area underlying the electrode.

Conventional electrodes of this type typically have a support layer with an adhesive underside which supports a conductive contact element in the form of a conductive male snap fastener element. The bottom face of the snap fastener element is exposed at the underside of the support layer while its tip projects from the top surface of the support layer so that the tip can be coupled to a female snap fastener element connected by an electrical lead to the monitoring equipment.

The support layer also supports a resilient pad impregnated with a conductive gel. The upper surface of the pad makes good conductive contact with the underside of the snap fastener element and when the support layer is adhered to the patient's body, the underside of the gel pad makes good conductive contact with the skin area against which it is pressed.

One problem encountered with the prior medical electrodes of this general type is corrosion of the part of the snap fastener element contacted by the gel pad. This corrosion results because the electrolyte gel in the pad often contains salts which corrode the metal in the fastener element. The corrosion, in turn, gives rise to noise artifacts in the signal coupled by the electrode to the monitoring equipment and increases the impedance of the electrode.

To overcome this problem, prior electrodes employ a snap fastener element whose eyelet is made of noncorroding silver or which is made entirely of silver. This has proved to be a relatively expensive solution to the corrosion problem because of the high cost of silver today.

In an attempt to achieve the same results at lower cost, one prior electrode we are aware of has a snap fastener element made entirely of plastic which is then silver coated. In other words, the fastener rivet stud and eyelet are separately molded plastic pieces which are then coated with silver. When the plastic stud and eyelet are press-fit together, the silver coating thereon does provide a reasonably good conductive path between the gel pad and the mating snap fastener element leading to the monitoring equipment.

However, in a given monitoring application, it may be necessary to repeatedly connect the monitoring equipment to the snap fastener element on the electrode because the patient is being moved or because it is necessary to connect a particular electrode to different pieces of equipment. In fact, when meeting specifications, it is often necessary to guarantee that the electrode will be able to withstand a specified number of connect and disconnect operations, e.g. six, without any material change in its impedance or d.c. offset. The electrodes employing the aforesaid silver-plated plastic fastener elements sometimes fail to meet this test. This is because the repeated connections to the fastener stud abrades the silver coating thereon. Moreover, those prior plated fastener elements are still relatively expensive because of the amount of silver on them.

Another factor which adversely affects the impedance characteristics of prior electrodes involves loss of electrolyte gel which sometimes occurs when the electrode is adhered to the patient's body. More particularly, when adhering the electrode, or connecting its contact element, the resilient gel pad is compressed against the skin, with the result that some of the gel is squeezed out of the pad and along the skin. Then when the pad resumes its unstressed condition, there may be some loss of gel at the boundary between the gel pad and the snap fastener element so that there is no longer good conductive contact between the element and pad.

Attempts to overcome this problem have involved forming a rigid wall around the gel pad. When the electrode is adhered to the patient's body, the wall is pressed against the skin and acts as a barrier to prevent the gel from being squeezed out of the pad. An example of this type of electrode is described in U.S. Pat. No. 3,838,766.

While this rigid wall does contain the electrolyte gel, it also causes patient discomfort because it makes the electrode as a whole relatively rigid and nonconforming. It also bears against the skin and becomes irritating, particularly to an infant or a patient with particularly tender skin. Such electrodes have other disadvantages fully described in the aforesaid patent. Furthermore, they have a relatively high profile, making them rather bulky and prone to catch on objects that might strip the electrode from the patient's body.

SUMMARY OF THE INVENTION

Accordingly, the present invention aims to provide an improved medical electrode which has good impedance characteristics.

The further object of the invention is to provide a disposable medical electrode which is relatively inexpensive to make.

Yet another object of the invention is to provide an electrode of this general type which maintains a good conductive path between the patient's skin and a contact element leading to apparatus for monitoring signals from the patient.

A further object is to provide an electrode of the pregelled disposable type which has a relatively low profile, yet contains a relatively large gel pad.

Another object of the invention is to provide a medical electrode which is relatively comfortable to wear even for a prolonged period.

Other objects will in part be obvious and will in part appear hereinafter.

The invention accordingly comprises the features of construction, combination of elements and arrangement of parts which will be exemplified in the following detailed description, and the scope of the invention will be indicated in the claims.

In brief, the electrode of this invention comprises a thin compliant support layer, the undersurface of which is adhesive. An opening extends through the layer and a flexible resilient collar projects from the underside of the support layer all around the opening. The support layer supports a snap contact element in the form of a metallic rivet stud and a silver-coated plastic eyelet press-fit into the stud. The underside of the eyelet is exposed in the opening in the support layer and the tip of the metallic stud projects from the top of that layer. A resilient pad impregnated with an electrolyte gel is snugly received in the opening and collar. The upper surface of the pad is in conductive contact with the underside of the silver-coated plastic eyelet, while the underside of the pad is exposed at the rim of the collar at the underside of the support layer.

Since the eyelet which is the only fastener part in contact with the gel pad is silver-coated, any salt in the gel does not tend to corrode the contact element and thus upset the conductivity and impedance characteristics of the electrode. Yet, utilization of a standard metallic snap fastener rivet stud reduces the overall cost of the electrode and also insures that repeated connections can be made to the electrode without degrading the signal from the patient's body.

Furthermore, the flexible, resilient collar surrounding the gel pad at the underside of the electrode retains the gel in the pad so that there is intimate conductive contact between the coated plastic eyelet and the pad even when the electrode is adhered to the patient's body. Also, the collar helps to maintain the electrode in a wet conductive condition even when the underside of the gel pad is exposed for a relatively long period of time.

BRIEF DESCRIPTION OF THE DRAWING

For a fuller understanding of the nature and objects of the invention, reference should be had to the following detailed description taken in connection with the accompanying drawing, in which:

FIG. 1 is an isometric view of an improved electrode made in accordance with this invention applied to a patient's body;

FIG. 2 is an exploded perspective view on a larger scale showing the elements of the electrode in greater detial; and FIG. 3 is a fragmentary cutaway view of the electrode on a still larger scale.

DESCRIPTION OF THE PREFERRED EMBODIMENT

Referring now to FIG. 1 of the drawing, the subject electrode is shown generally at 10 adhered to a patient's body 12. The electrode provides a good conductive path between a skin area underlying the electrode 10 and an electrical contact element in the form of a conductive snap contact element 14 projecting from the top of the electrode.

Monitoring apparatus (not shown) is connected to the electrode by means of its electrical lead 16 which terminates in a mating conductive snap element 18 coupled to element 14.

As seen from FIG. 1, electrode 10 conforms to the contour of the body and has a low profile so that it does not tend to catch on nearby objects. Furthermore, it is small and lighweight so that it does not cause undue patient discomfort even when worn for a relatively long period of time.

Referring now to FIGS. 2 and 3, the electrode 10 comprises a soft, compliant discoid support layer 22 preferably made of closed cell plastic foam material such as polyurethane or polyethylene plastic. In the illustrated embodiment, layer 22 has a diameter of 2 inches and is about ⅛ inch thick. Also, the bottom surface 22a of layer 22 is provided with a conventional medical adhesive coating 23.

As best seen in FIG. 3, a circular opening 24 is formed in layer 22 extending between its top surface 22b and bottom surface 22a. Opening 24 is centered on layer 22 and is typically on the order of ⅝ inch in diameter.

A ring-shaped collar 26 projects from the surface 22a of layer 22 and extends all around the mouth of opening 24. The barrier 26 is made of a flexible, resilient material such as the closed cell plastic foam material noted above. The collar can be a separate piece adhered to the underside of layer 22 by means of adhesive coating 23. Alternatively, layer 22 and collar 26 can be formed as a unit. The inside diameter of barrier 23 is the same as that of opening 24 and it has a wall thickness on the order of ⅛ inch and is typically 1/16 inch high.

Opening 24 (including its extension through collar 26) snugly receives a soft, compliant pad 28 in the form of a small disk of open cell plastic foam material such as open cell polyurethane plastic. In use, pad 28 is impregnated with a conventional conductive electrolyte gel such as Redux Creme or any other conveniently available medical conductive gel. The diameter of pad 28 is substantially the same as that of opening 24 and the pad extends from the upper surface 22b of layer 22 to the rim 26a of collar 26 or slightly beyond so that, in its uncompressed state, pad 28 projects slightly below the rim as illustrated in FIG. 3. Since the pad 28 extends entirely through layer 22, it is larger than usual and can thus contain a maximum amount of gel.

Snap contact 14 is actually composed of two parts, to wit: a standard metallic rivet stud 14a and a plastic eyelet 14b which is arranged to be press-fit into stud 14a. Eyelet 14b has a thin coating 34 of silver metal or other conductive material that is not affected by the gel in pad 28.

The tip of eyelet 14b is inserted through an opening 32a at the center of a thin, impervious discoid plastic sheet 32 and then the stud 14a is press-fit down onto the eyelet with the sheet 32b sandwiched between those two elements. Finally, sheet 32 which is somewhat smaller than layer 22, is adhered to the top surface 22b of that layer so that the underside of eyelet 14b is centered on the upper face of pad 28.

With this construction, a standard metallic rivet stud 14a can be employed without any problem of its being corroded by electrolyte gel. This is because the eyelet 14b is interposed between the stud and gel pad 28. Since the rivet stud 14a is made of a strong solid material such as steel, its conductive characteristics are not affected by repeated connections to its mating fastening element 18 (FIG. 1). On the other hand, the plastic eyelet is unaffected by the gel and its silver coating 24 provides an excellent conductive path between the electrolyte in pad 28 and the rivet stud 14a.

In use, the electrode 10 is pressed against an appropriate location on the patient's body so that its support layer 22 adheres to the skin. Then the snap fastener element 18 is snapped onto element 14. Normally, the force exerted on the electrode when adhering it to the skin and/or attaching fastener 18 applies sufficient pressure to pad 28 to squeeze gel from the pad. In the present instance, however, the ring-shaped, closed cell foam collar 26 which surrounds pad 28 is also pressed against the patient's skin so that the gel is trapped within the pad. Resultantly, all portions of the pad remain in a wet conductive condition, particularly the portion abutting eyelet 14*b*.

Thus, the collar 26 contributes stability to the gel area, resulting in reduced electrical noise in the signal originating in the body. Still, however, because the barrier 26 is made of a soft, lightweight, flexible, resilient material, there are no hard or rigid surfaces presented to the patient's skin. Consequently, the patient can wear the electrode for a relatively long period without discomfort.

Usually, disposable electrodes of this general type are pregelled and then stored until needed. Accordingly, a strippable cover (not shown) is adhered to the undersurface 22*a* of layer 22 to protect the adhesive coating 23 and to cover the exposed underside of pad 28. A typical cover is shown in the above patent. Any suitable cover material such as vinyl plastic may be used for this purpose.

As noted previously, the top surface of pad 28 is covered by the impervious vinyl sheet 32, while the sides of the pad are covered by the closed cell foam of layer 22 and collar 26. Therefore, when the cover (not shown) is present, the pad remains in a wet conductive condition for a long time. However, even when the cover is removed, the pad remains wet for a reasonable time because drying only occurs at its exposed underside.

It will thus be seen that the present electrode provides a good electrical connection between a patient's body and monitoring equipment. Because it is small, lightweight, and made substantially entirely of a soft compliant material, it conforms well to the patient's body and is comfortable to wear. In fact, the only rigid element in the electrode is the fastener element 14 which is completely isolated from the patient's body. Also, the unique metal-coated plastic eyelet construction results in a savings in initial materials costs without any appreciable sacrifice in the electrical characteristics of the electrode. Finally, the present construction maintains a large stable gel area during the application and connection of the electrode so that there is less need to replace electrodes because of excessive noise artifacts.

It will also be seen that the objects set forth above, among those made apparent from the preceding description, are efficiently attained and, since certain changes may be made in the above construction without departing from the scope of the invention, it is intended that all matter contained in the above description or shown in the accompanying drawing shall be interpreted as illustrative and not in a limiting sense.

It should be understood, too, that the following claims are intended to cover all of the generic and specific features of the invention herein described.

I claim:
1. A medical electrode comprising
   A. a flexible support layer having a top surface and an adhesive bottom surface,
   B. means defining a through opening in the support layer extending between its top and bottom surfaces,
   C. a flexible, resilient collar
      1. projecting from the bottom surface of the support layer, and
      2. surrounding said opening,
   D. a thin nonporous sheet
      1. adhered to the top surface of the support layer, and
      2. covering a substantial portion of said opening,
   E. a gel pad snugly received in said opening and collar, said gel pad having a top surface contacting the nonporous sheet and a bottom surface exposed at the rim of said collar, and
   F. a conductive contact element
      1. supported by the nonporous sheet,
      2. having a first portion thereof in conductive contact with the top surface of the gel pad, and
      3. having a second portion thereof projecting above the nonporous sheet.
2. The electrode defined in claim 1 wherein the support layer and collar are formed of a closed cell plastic foam material.
3. The electrode defined in claim 1 wherein the contact element is a snap fastener element, the second portion of said contact element comprising
   A. a metallic rivet stud, and the first portion of said contact element comprising
   B. a plastic eyelet, said eyelet
      1. being coated with an electrically conductive material which is compatible with gel in the gel pad,
      2. having a portion thereof contacting the gel pad, and
      3. being coupled to the rivet stud so as to provide a conductive path between the gel in the gel pad and the rivet stud.
4. The electrode defined in claim 3 wherein the conductive material is silver metal.
5. A medical electrode comprising:
   A. a flexible, resilient support layer having a top surface and an adhesive bottom surface,
   B. means defining a through opening in the support layer extending between its top and bottom surfaces,
   C. a gel pad,
      1. supported by the support layer, and
      2. having a portion thereof exposed at the bottom surface of the support layer,
   D. an electrical contact element
      1. supported by the support layer, and
      2. comprising a snap fastener element including
         a. a conductive metallic rivet stud projecting from the top surface of the support layer, and
         b. a non-conductive, non-metallic eyelet
            i. coated with an electrically conductive material which is compatible with gel in said gel pad,
            ii. coupled to the stud, and
            iii. having a portion thereof contacting the gel pad so as to provide a conductive path between the gel in the gel pad and the stud,
   E. a thin, non-porous sheet,
      1. sandwiched between the rivet stud and eyelet so as to prevent the gel in said gel pad from contacting the rivet stud, and
      2. adhered to the top surface of the support layer, and
   F. wherein the gel pad is received in the opening through the support layer so that
      1. its upper surface contacts the coated eyelet, and
      2. its lower surface is exposed at the bottom surface of the support layer.
6. The electrode defined in claim 5 wherein the conductive material comprises metallic silver.
7. The electrode defined in claim 5
   A. wherein the gel pad projects appreciably below the bottom surface of the support layer, and
   B. further including
      1. a flexible, resilient collar projecting below the bottom surface of the support layer, more or less even with the gel pad, and
      2. extending all around said opening so as to surround said gel pad.

* * * * *